(12) United States Patent
Belter

(10) Patent No.: US 7,786,334 B2
(45) Date of Patent: Aug. 31, 2010

(54) CATALYTIC PROCESS FOR THE PREPARATION OF FLUORINATED HALOCARBONS

(76) Inventor: Randolph K. Belter, 14400 Williams Blvd., Zachary, LA (US) 70791

( * ) Notice: Subject to any disclaimer, the term of this patent is extended or adjusted under 35 U.S.C. 154(b) by 0 days.

(21) Appl. No.: 12/383,126

(22) Filed: Mar. 20, 2009

(65) Prior Publication Data

US 2009/0182178 A1  Jul. 16, 2009

Related U.S. Application Data

(62) Division of application No. 11/825,735, filed on Jul. 9, 2007, now abandoned.

(51) Int. Cl.
*C07C 17/20* (2006.01)
(52) U.S. Cl. .................. 570/165; 570/134; 570/170
(58) Field of Classification Search .............. 570/134, 570/165, 170
See application file for complete search history.

(56) References Cited

U.S. PATENT DOCUMENTS

| 4,158,675 A | 6/1979 | Potter |
| 4,967,024 A | 10/1990 | Gumprecht et al. |
| 5,185,482 A | 2/1993 | Manzer |

OTHER PUBLICATIONS

Belter et al, Journal of Fluorine Chemistry, 127, 2006, 1606-1610.*

* cited by examiner

*Primary Examiner*—Shailendra Kumar
(74) *Attorney, Agent, or Firm*—Richard J. Hammond

(57) ABSTRACT

A process is described for the preparation of 2-chloro-1,1,1-difluoroethane by the reaction of 1,2-dichloro-1,1-difluoroethane with hydrogen fluoride. in the presence of a fluorination catalyst. The process utilizes a rate enhancing reagent that is trichloroethylene, is 1-fluoro-1,2,3-trichloroethane or an aromatic rate enhancing reagent having the formula

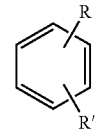

where R is $C_1$ to $C_6$ linear or branched alkyl substituted with at least one halo group, halo or nitro and R' is $C_1$ to $C_6$ linear or branched alkyl substituted with at least one halo group.

7 Claims, No Drawings

US 7,786,334 B2

CATALYTIC PROCESS FOR THE PREPARATION OF FLUORINATED HALOCARBONS

This application is a divisional of U.S. application Ser. No. 11/825,735, filed on Jul. 9, 2007, now abandoned, incorporated herein by reference

FIELD OF INVENTION

The present invention relates to a process for the preparation of chlorofluoro ethanes. More particularly, a process for the preparation of 2-chloro-1,1,1-trifluoroethane is described that utilizes rate enhancing reagents.

DESCRIPTION OF THE RELATED ART

For decades chlorofluorocarbons have been useful chemicals for refrigeration, solvent, foam manufacture and firefighting applications. The refrigerant R-12 (difluorodichloroethane) was the standard refrigerant and found widespread use in automotive air conditioners. The discovery of the harmful nature of chlorofluorocarbons towards the Earth's protective ozone layer led to the outlawing of the manufacture and use of most of these chemicals in the 1989 Montreal Protocol. The most popular non-ozone depleting replacement for R-12 for use in automotive air conditioning units has been R-134a (1,1,1,2-tetrafluoroethane).

The production of R-134a generally begins with trichloroethylene (TCE) as feedstock for a two step process. The first reaction is typically performed under catalytic conditions to produce 2-chloro-1,1,1-trifluoroethane (R-133a). This can be done in the liquid or vapor phase. In the second reaction, R-133a is further fluorinated to R-134a. See, for example, U.S. Pat. No. 5,185,482. As this second reaction is more difficult, it is most successfully performed as a high temperature vapor phase reaction over an alumina or chromia catalyst.

The first reaction can be broken down into three individual steps (see Scheme 1, Reaction 1). In a First step, a molecule of hydrogen fluoride (HF) adds across the TCE double bond to produce 1-fluoro-1,1,2-trichloroethane (R-131a). As a Second step, direct fluorine-for-chlorine exchange converts R-131a to 1,2-dichloro-1,1-difluoroethane (R-132b). Finally, in the Third step another fluorine-for-chlorine exchange occurs that converts R-132b to R-133a. Note, hydrogen chloride is also produced in each of these reaction steps.

SCHEME 1

Reaction 1

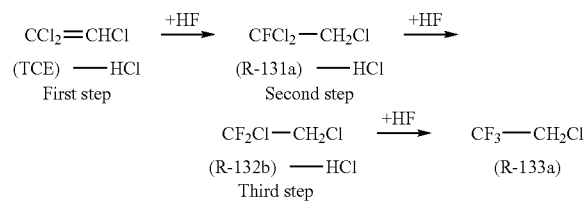

Reaction 2

In the typically vapor phase subsequent reaction, R-133a is converted to R-134a. See Scheme 1, Reaction 2.

In the liquid phase reaction of TCE to R-133a, many transition metal halide Lewis acid catalysts have been reported to be effective. For example, the antimony (V) halides are the benchmark catalysts for fluorine-for-chlorine exchange (Swartz reaction). However they are disadvantageously reduced to Sb (III) at temperatures above 80 C. The prior art indicates that tantalum (V) halides and niobium (V) halides are the best choices for TCE to R-133a conversion. See, for example, U.S. Pat. No. 4,967,024.

SUMMARY OF THE INVENTION

A process is described for the preparation of 2-chloro-1,1,1-trifluoroethane by the reaction of 1,2-dichloro-1,1-difluoroethane with hydrogen fluoride, in the presence of a fluorination catalyst. The process utilizes a rate enhancing reagent that is trichloroethylene, is 1-fluoro-1,1,2-trichloroethane or an aromatic rate enhancing reagent having the formula

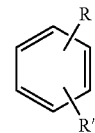

where R is $C_1$ to $C_6$ linear or branched alkyl substituted with at least one halo group, halo or nitro and R' is $C_1$ to $C_6$ linear or branched alkyl substituted with at least one halo group.

DETAILED DESCRIPTION OF THE INVENTION

As noted in the above description of the prior art, the process for the preparation of 1,1,1,2-tetrafluoroethane (R-134a) by the catalyzed, liquid phase reaction of hydrogen fluoride with trichloroethylene (TCE) has been studied extensively. The typically isolated intermediate in the reaction is 2-chloro-1,1,1-trifluoroethane (R-133a). However, it has not been realized that TCE itself as well as 1,1,2-dichloro-1-fluoroethane (R-131a) are rate enhancing reagents (additives) that promote the catalyzed, hydrogen fluoride reaction of 1,2-dichloro-1,1-difluoroethane (R-132b), and mixtures containing 1,2-dichloro-1,1-difluoroethane (R-132b), to yield R-133a. In fact, it has now been discovered that the catalyzed, hydrogen fluoride reaction of 1,2-dichloro-1,1-difluoroethane (R-132b) to yield R-133a proceeds at a disadvantageously slow rate if these rate enhancing reagents are not present.

In one preferred embodiment of the present invention the preparation of R-133a by the reaction of hydrogen fluoride with R-132b in the liquid phase using a hydrofluorination catalyst, e.g., a metal halide, is promoted by the addition of a rate enhancing amount of trichloroethylene or 1,1,2-trichloro-1-fluoroethane (R-131a). The most preferred catalyst in these liquid phase reactions is tantalum (V) halides, e.g., tantalum fluoride, chloride or bromide. However, niobium (V) halides and other rare earth halide catalysts may also be used in this conversion of R-132b to R-133a.

Typically, the amount of trichloroethylene (TCE) or of 1,1,2-trichloro-1-fluoroethane (R-131a) is the ratio of from about 0.1:1 to about 1.5:1 TCE:R-132b or R-131a:R-132b by volume. Preferably the ratio is from about 0.1:1 to 1:1 TCE:R-132b or R-131a:R-132b, most preferably 0.25:1 TCE:R-132b or R-131a:R-132b.

The process of the present invention is carried out at a temperature of from about 100° to about 175° C., preferably 125° to about 160° C., most preferably at 140° C.

A further preferred embodiment of the present invention relates the discovery of aromatic rate enhancing reagents for the catalyzed reaction of hydrogen fluoride (HF) with 1,2-dichloro-1,1-difluoroethane (R-132b) to produce 2-chloro-1,1,1-trifluoroethane (R-133a).

These aromatic reagents have the formula

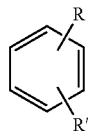

where R is $C_1$ to $C_6$ linear or branched alkyl substituted with at least one halo group, halo or nitro and R' is $C_1$ to $C_6$ linear or branched alkyl substituted with at least one halo group.

Preferably halo is fluoro or chloro, most preferably fluoro. Preferably alkyl is $C_1$ to $C_4$ linear or branched alkyl, most preferably methyl or ethyl.

Preferably R and R' are the same and are $C_1$ to $C_4$ linear or branched alkyl substituted with at least one halo group, most preferably trifluoromethyl Typically, the amount of the aromatic rate enhancing additive is from about 0.01:1 to about 1.5:1 aromatic rate enhancing reagent:R-132b by volume. Preferably the ratio is from about 0.1:1 to 0.5:1 aromatic rate enhancing reagent:R-132b, most preferably 0.15:1 aromatic rate enhancing reagent:R-132b.

As disclosed herein, the process for the preparation of 1,1,1,2-tetrafluoroethylene (R-134a) generally begins with TCE as a feedstock in a liquid phase, catalyzed, hydrofluorination reaction. For every liquid phase fluorination reaction, a certain amount of oligomerization occurs, evidenced by the formation of higher boiling liquid or semi-liquid by-products. Such by-products, referred to as "oligomeric tars", accumulate in greater amounts when starting materials, reaction products and\or reaction by-products are unsaturated compounds. Thus, when the conversion of TCE to R-133a, is carried out in a single step reaction, relatively large amounts of tars are produced. This is largely because of the unsaturated staring material, TCE. If the reaction is halted at the first intermediate (see Scheme 1, Reaction 1, First Step), and any subsequent reactions carried out in one or more steps, i.e., R-131a to R-132b then R-132b to R-133a (see Scheme 1, Reaction 1, Second Step and Third Step) a lesser amount of tars are produced, i.e., these reactions do not proceed through an olefinic intermediate thereby almost eliminating tar formation. It has now been discovered that an improved process for the manufacture of R-133a from the starting material TCE can be advantageously effected by carrying out the hydrofluorination reaction of trichloroethylene (TCE) at as low a temperature as possible, e.g. from about −5° to about 30° C., thereby producing a reaction mixture comprising 1,1,2-trichloro-1-fluoroethane that is substantially free of TCE.

Typically, the ratio of trichloroethylene (TCE) to hydrogen fluoride is from about 1:0.1.5 to about 1.0:1.2 by volume. Preferably the ratio is from about 1.0:1 to 0.9:1.0 TCE:HF, most preferably 0.8:1.0 TCE:HF The reaction is performed for a time sufficient to substantially reduce the trichloroethylene concentration and produce R-131a in good yields. Subsequent hydrofluorination of R-131a may then be continued in the same or a different vessel, using the same or a different catalyst charge, while increasing the temperature to about 100° to about 175° C., preferably 125° to about 160° C., most preferably at 140° C.

The reaction is readily conducted using ratios of HF somewhat greater than R-131a. A reaction stream comprising 2-chloro-1,1,1-trifluoroethane (R-133a) is produced by this technique substantially free of oligomeric tars.

The present invention is illustrated by the following examples.

EXAMPLES

Example 1

Hydrofluorination of
1,2-dichloro-1,1-difluoroethane—Without Rate
Enhancing Reagent Seven Hundred and twenty milligrams (0.002 mol) of tantalum pentachloride ($TaCl_5$) was charged into a 250 milliliter reactor. The reactor was evacuated and cooled with ice. Fifty grams (2.5 moles) of anhydrous hydrogen fluoride (HF) was next added to the reactor. The resulting solution was heated with stirring to 140° C. for 60 minutes. The reactor was cooled with ice and 13.4 grams (0.1 mol) of 1,2-dichloro-1,1-difluoroethane (R-132b) was added. The reactor was heated to 140° C. and samples were withdrawn from the reactor headspace. The reaction was monitored by GC. After 1.5 hours, a sample was analyzed. The yield of 2-chloro-1,1,1-trifluoroethane (R-133a) was 36.5%. A repeat example using the same amount of reactants under the same conditions produced a yield of R-133a of 22%.

Example 2

Hydrofluorination of
1,2-dichloro-1,1-difluoroethane—15% Rate
Enhancing Reagent Added Seven Hundred and twenty milligrams (0.002 mol) of tantalum pentachloride ($TaCl_5$) was charged into a 300 milliliter reactor. The reactor was evacuated and cooled with ice. Fifty grams (2.5 moles) of anhydrous hydrogen fluoride (HF) was next added to the reactor. The resulting solution was heated with stirring to 140° C. for 60 minutes. The reactor was cooled with ice and a mixture of 13.4 grams (0.1 mol) of 1,2-dichloro-1,1-difluoroethane (R-132b) and 2.2 grams (0.015 mole) 1-fluoro-1,1,2-trichloroethane (R-133a) was added. The reactor was heated to 130° C. and samples were withdrawn from the reactor headspace. The reaction was monitored by GC. After 1 hour a sample was analyzed. The yield of 2-chloro-1,1,1-trifluoroethane (R-133a) was 87.5%.

Example 3

Hydrofluorination of Trichloroethylene—Without
Rate Enhancing Reagent

In a 500 milliliter Hastaloy reactor was placed 7.2 grams of $TaF_5$. The reactor was evacuated, cooled in an ice bath and 120 grams (6 mol) of anhydrous HF were added. The reactor was heated to 100° C. and 131 grams (1 mol) trichloroethylene were added all at one time. The reactor was then rapidly heated to 140° C. and maintained at this temperature for 6 hours. A constant pressure of 500 psi was maintained by venting the hydrogen chloride reaction product. At the conclusion of the reaction period, the contents of the reactor were vented into crushed ice. Analysis of the product obtained from the ice mixture gave a yield of 2-chloro-1,1,1-trifluoroethane of 80%. The residue in the reactor was extracted with 10% hydrochloric acid. The amount of residue was 13 grams and appeared to be a water insoluble oligomeric tar

Example 4

Hydrofluorination of Trichloroethylene—With Rate Enhancing Reagent

In a 500 milliliter Hastaloy reactor was placed 7.2 grams of $TaF_5$. The reactor was evacuated, cooled in an ice bath and 120 grams (6 mol) of anhydrous HF were added. Next were added 131 grams (1 mol) trichloroethylene slowly to the cold HF solution over a 30 minute period and the reactor contents rapidly stirred for an additional two hours at about 5° C. The reactor was then allowed to warm to room temperature over about two hours. Samples of the reaction product after this time showed that only traces of trichloroethylene remained, the majority of the reaction product being 1-fluoro-1,1,2-trichloroethane (R-131a). The reactor was then heated to 140° C. and maintained at that temperature for about 6 hours. Pressure was maintained at 500 psi by venting the hydrogen chloride reaction product. At the conclusion of the reaction period, the contents of the reactor were vented into crushed ice. Analysis of the product obtained from the ice mixture gave a yield of 2-chloro-1,1,1-trifluoroethane of 90%. The residue in the reactor was extracted with 10% hydrochloric acid. The amount of residue was 5 grams and appeared to be a water insoluble oligomeric tar.

Example 5

Hydrofluorination of R-132b—15% Trichloroethylene Rate Enhancing Reagent

Seven hundred and twenty milligrams (0.004 mol) of TaCl5 was charged to the reactor. The reactor was evacuated and cooled with ice. Fifty grams (2.5 mol) of anhydrous hydrogen fluoride was charged. The solution was heated with stirring to 140° C. for 1 h. The reactor was again cooled with ice. A mixture of 13.4 g. (0.1 mol) 1,2-dichloro-1,1difluoroethane and 1.97 g (0.15 mol) trichloroethylene was injected and the reactor heated to 140° C. Samples were drawn from the reactor headspace and the reaction was monitored by GC. Conversion at 1 hour was 75%.

Examples 6-11

Hydrofluorination of R-132b in the Presence of Equal Volume Solvent Enhancer Seven hundred and twenty milligrams (0.004 mol) of TaCl5 was charged to the reactor. The reactor was evacuated and cooled with ice. Fifty gram (2.5 mol) of anhydrous hydrogen fluoride was charged. The solution was heated with stirring to 140° C. for 1 h. the reactor was again cooled with ice. A mixture of 13.4 g (0.1 mol) 1,2-dichloro-1,1-difluoroethane and 10 mL of the chosen solvent was injected and the reactor heated to 140° C. Samples were drawn from the reactor headspace and the reaction was monitored by GC. See Table 1 for results.

TABLE 1

R-132b to R-133a conversion with equal volumes of rate enhancing reagents

| Reagent | % conversion 1 hour | % conversion 2 hours | % conversion 3 hours |
| --- | --- | --- | --- |
| TCE | 92 | 98 | 100 |
| m-$CF_3$—Ph—$CF_3$ | 97 | 100 | 100 |
| p-$CF_3$—Ph—$CF_3$ | 93 | 100 | 100 |
| m-F—Ph—$CF_3$ | 72 | 78 | 83 |
| m-Cl—Ph—$CF_3$ | 66 | 71 | 90 |
| p-Cl—Ph—$CF_3$ | 45 | 54 | 63 |

Example 12-17

Hydrofluorination of R-132b in the Presence of 15% Volume Solvent Enhancer

Seven hundred and twenty milligrams (0.004 mol) of TaCl5 was charged to the reactor. The reactor was evacuated and cooled with ice. Fifty grams (2.5 mol) of anhydrous hydrogen fluoride was charged. The solution was heated with stirring to 140° C. for 1 h. The reactor was again cooled with ice. A mixture of 13.4 gm (0.1 mol) 1,2-dichloro-1,1-difluoroethane and 1.5 mL the chosen solvent was injected and the reactor heated to 140° C. Samples were drawn from the reactor headspace and the reaction was monitored by GC. See Table 2 for results.

TABLE 2

R-132b to R-133a conversion with a 15% volume of aromatic rate enhancing reagents

| Reagent | % conversion 1 hour | % conversion 2 hours | % conversion 3 hours |
| --- | --- | --- | --- |
| TCE | 75 | 86 | 91 |
| m-$CF_3$—Ph—$CF_3$ | 70 | 82 | 93 |
| p-$CF_3$—Ph—$CF_3$ | 70 | 85 | 90 |
| m-F—Ph—$CF_3$ | 72 | 80 | 85 |
| m-Cl—Ph—$CF_3$ | 70 | 88 | 90 |
| p-Cl—Ph—$CF_3$ | 68 | 80 | 82 |

I claim:

1. In a process for the preparation of 2-chloro-1,1,1-trifluoro by the reaction of 1,2-dichloro-1,1-difluoroethane and mixtures containing 1,2-dichloro-1,1-difluoroethane with hydrogen fluoride in the presence of a fluorination catalyst, the improvement comprising adding to said reaction a rate enhancing reagent that is an aromatic rate enhancing reagent having the formula

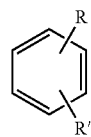

where R is $C_1$ to $C_6$ linear or branched alkyl substituted with at least one halo group, halo or nitro and R' is $C_1$ to $C_6$ linear or branched alkyl substituted with at least one halo group.

2. In the process according to claim 1 wherein R and R' are the same and are $C_1$ to $C_6$ linear or branched alkyl substitute with at least one halo group.

3. In the process according to claim 1 wherein R and R' are the same and are $C_1$ to $C_4$ linear or branched alkyl substituted with at least one halo group.

4. In the process according to claim 1 wherein R and R' are trifluoromethyl.

5. In the process according to claim 1 wherein the ratio of the amount of rate enhancing reagent is from about 0.1:1 to about 1.5:1 rate enhancing reagent: 1,2-dichloro-1,1-difluoroethane by volume.

6. In the process according to claim 5 wherein the ratio is from about 0.1:1 to about 1:1 rate enhancing reagent: 1,2-dichloro-1,1-difluoroethane by volume.

7. In the process according to claim 6 wherein the ratio is from about 0.1:1 to about 0.25:1 rate enhancing reagent: 1,2-dichloro-1,1-difluoroethane by volume.

* * * * *